United States Patent [19]

Bahrmann et al.

[11] Patent Number: 5,118,867
[45] Date of Patent: Jun. 2, 1992

[54] PROCESS FOR THE PREPARATION OF ALDEHYDES

[75] Inventors: Helmut Bahrmann, Hamminkeln; Bernhard Fell; Georgios Papadogianakis, both of Aachen, all of Fed. Rep. of Germany

[73] Assignee: Hoechst Aktiengesellschaft, Fed. Rep. of Germany

[21] Appl. No.: 632,464

[22] Filed: Dec. 21, 1990

[30] Foreign Application Priority Data

Dec. 23, 1989 [DE] Fed. Rep. of Germany ....... 3942954

[51] Int. Cl.$^5$ .............................................. C07C 45/50
[52] U.S. Cl. .................................. 568/454; 568/449; 568/451; 568/452; 568/455
[58] Field of Search ............... 568/449, 451, 452, 454, 568/455

[56] References Cited

U.S. PATENT DOCUMENTS

| | | | |
|---|---|---|---|
| 4,330,678 | 5/1982 | Van Leeuwen et al. | 568/454 |
| 4,467,116 | 8/1984 | Van Leeuwen et al. | 568/454 |

FOREIGN PATENT DOCUMENTS

| | | | |
|---|---|---|---|
| 0096986 | 12/1983 | European Pat. Off. | 568/454 |
| 0096987 | 12/1983 | European Pat. Off. | 568/454 |
| 0096988 | 12/1983 | European Pat. Off. | 568/454 |
| 0149894 | 7/1985 | European Pat. Off. | 568/454 |
| 254937 | 2/1988 | European Pat. Off. | |
| 268268 | 5/1988 | European Pat. Off. | |

Primary Examiner—Werren B. Lone
Attorney, Agent, or Firm—Jordan B. Bierman

[57] ABSTRACT

The preparation of aldehydes by hydroformylation of olefinically unsaturated compounds. The reaction is carried out in the presence of a catalyst system which contains rhodium and an ammonium salt of a sulfonated phosphorous acid triester which is soluble in organic media.

29 Claims, No Drawings

PROCESS FOR THE PREPARATION OF ALDEHYDES

This Application claims the priority of German Application P 39 42 954.7, filed Dec. 23, 1989.

The present invention relates to a process for the preparation of aldehydes by reaction of olefinic compounds with hydrogen and carbon monoxide at elevated temperatures under increased pressure in a homogeneous phase. The reaction is carried out in the presence of a catalyst system containing rhodium and an organic phosphorus compound, the organic phosphorus compound being an ammonium salt, which is soluble in organic media, of a sulfonated phosphorous acid triester.

BACKGROUND OF THE INVENTION

It is known that aldehydes and alcohols can be prepared by reaction of olefins with carbon monoxide and water. This reaction, which is called hydroformylation (oxo synthesis), is generally catalyzed by hydridometalcarbonyls, preferably those which are derived from metals of group VIIIA of the Periodic Table (IUPAC Version).

In addition to cobalt, which is widely used industrially as the catalyst metal, rhodium has recently been acquiring increasing importance. In contrast to cobalt, rhodium enables the reaction to be carried out under a low pressure; moreover, straight-chain aldehydes are preferentially formed, and branched aldehydes are formed to only a minor degree. Finally, hydrogenation of the olefins to give saturated hydrocarbons is significantly lower when rhodium catalysts are used than when cobalt catalysts are used. In the processes introduced in industry, the rhodium catalyst is employed in the form of modified hydridorhodiumcarbonyls, which additionally contain, in excess if appropriate, ligands. Tertiary organic phosphines and phosphites have proven to be particularly suitable ligands.

The catalyst system consisting of $HRh(CO)(PPh_3)_3$ and excess $PPh_3$ ($Ph=C_6H_5$) is thus employed, for example, for hydroformylation of alpha-olefins, such as ethylene, propylene and butene-1 at temperatures between 90° and 120° C. This system and reaction are disclosed in U.S. Pat. No. 3,527,809.

The outstanding suitability of the Rh/triphenylphosphine catalyst for the hydroformylation of alphaolefins is confirmed in European Patent 149,894 B1. At the same time, however, it is pointed out that the reaction of internal olefins such as butene-2 presents problems, because it leads to significant conversions only if higher temperatures are used. Under these conditions, however, isomerization of the olefin increases greatly. Some of the butene-2 is thus converted into butene-1, with the result that, in addition to the desired 2-methylbutyraldehyde, n-valeraldehyde is also formed to a considerable extent in the hydroformylation. At the same time, the activity and stability of the catalyst system also decrease, as is taught by European Patent 96, 987 B1 by the hydroformylation of butene-2. The rhodium/triphenylphosphine catalyst system is therefore unsuitable for the hydroformylation of internal olefins on an industrial scale.

The difficulties described above can be avoided if trialkyl or triaryl phosphites are employed as the catalyst component instead of trialkyl- or triarylphosphines. Organic phosphites in fact have the advantage that the hydroformylation of olefins proceeds at lower temperatures in their presence than if organic phosphines are used. Thus, according to Example 1 of European Patent 96,988 B1, butene-2 reacts with carbon monoxide and hydrogen under 2.86 MPa at 98.5° C. to give 2-methylbutyraldehyde using rhodium and cyclic phosphites as the catalyst.

German Specification 1,793,069 B2 describes the preparation of aldehydes by hydroformylation of olefins in the presence of rhodium compounds (which contain carbon monoxide bonded as a complex) and a triaryl, trialkyl or tricycloalkyl phosphite as the ligand, there being at least 2 mol of free ligand per g atom of rhodium present in the reaction medium. Examples therein relate both to the reaction of olefins and olefinically unsaturated compounds. Alkyl and aryl compounds are used as the phosphites.

The hydroformylation of 3.3-dialkoxy-1-propenes is the subject matter of German Specification 34 03 427 A1.

According to the procedure claimed, 3,3-diethoxybutanal and 2-methyl-3,3-diethoxypropanal are obtained in a molar ratio of 8.5 to 1 from for example 3,3-diethoxy-1-propene in the presence of Rh/triphenyl phosphite at 110° C. under a pressure of 0.3 MPa; the conversion is 99.5%.

According to European Patent 3,753 A1, rhodium, together with triphenyl phosphite, is likewise used as the catalyst in the reaction of cyclic acrolein acetals with carbon monoxide and hydrogen to give the corresponding aldehydes.

The hydroformylation of alpha, beta-unsaturated nitriles is described in U.S. Pat. No. 4,344,896. The reaction is carried out in the presence of rhodium which contains carbon monoxide, bonded as a complex, and, inter alia, an organic phosphorus compound. The phosphorus compound can be a phosphite, such as triphenyl phosphite, tri-4-tolylphosphite, tri-4-chlorophenyl phosphite, triethyl phosphite or tributyl phosphite.

Numerous publications relate to the use of specific phosphites as a constituent of hydroformylation catalysts.

The content of linear aldehydes as products of the hydroformylation of alpha- or beta-olefins is particularly high if rhodium complex compounds which contain fluorinated organic phosphites as ligands are employed as catalysts. This is taught in U.S. Pat. No. 4,330,678.

According to U.S. Pat. No. 4,467,116, less reactive olefins are hydroformylated in the presence of a catalyst which is a metal of group VIII A, modified, inter alia, by a triaryl phosphite as the ligand. At least one aryl radical of the phosphite is substituted by an optionally fluorinated alkyl group or by an aryl group.

Van Leeuwen and Roobeek in J. Organomet. Chem. 258 (1983), 343 et seq. also deal with the hydroformylation of non-reactive olefins, such as 2-methyl-1-hexene, limonene, cyclohexene and methylenecyclohexane. The reaction of such olefins under mild conditions (90° C. and 1 MPa) proceeds in the presence of rhodium catalysts modified by phosphite. Examples of the phosphite ligands employed are tris(o-t-butylphenyl) phosphite and tris-(hexafluoroisopropyl) phosphite; they are distinguished by specific steric and electronic properties.

Although the organic phosphites have a number of advantages over the organic phosphines as constituents of catalysts for the oxo synthesis, they are used to only a limited extent industrially. Their limited use is to be attributed to the fact that the activity of rhodium/phosphite catalysts decreases in the course of time, especially if they are used in the upper region of the particular temperature range recommended. At the same time, higher-boiling compounds are formed to an increased extent. Side reactions which convert the organic phosphite into inactive secondary products are at least partly the cause of both phenomena.

In this connection, it should be remembered that phosphorous acid triesters are very sensitive to hydrolysis. The traces of water formed by reduction processes during hydroformylation are sufficient to hydrolyze the triesters to di- and monoesters and to free phosphorous acid. Moreover, the acid mono- and diphosphites catalyze the hydrolysis of the triester, so that the reaction proceeds autocatalytically.

The rate of hydrolysis depends greatly on the nature of the ester radicals. Trimethyl phosphite is the most unstable and, as the length of the alkyl radicals increases, the phosphites become more resistant to hydrolysis. The activity of the catalyst system is furthermore impaired by the fact that the acid monoester is capable of protonating the rhodium/phosphite complex, i.e. converting it into a form which is likewise catalytically inactive.

The hydrolysis of the phosphorous acid ester can be prevented or at least certainly delayed by addition of organic or inorganic bases to the reaction mixture. According to the process of European Patent 285,136 A1, for example, secondary organic phosphites are removed selectively from solutions containing them together with tertiary organic phosphites by addition of an amine and removal of the ammonium phosphite formed. This procedure cannot be used unreservedly in the case of hydroformylation of olefinic compounds in the presence of rhodium/phosphite catalysts. It requires the addition of a substance foreign to the reaction to the reaction mixture, which can give rise to undesirable secondary reactions.

Further losses in phosphite may occur by reaction of the phosphorus compounds with aldehydes. As F. Ramirez demonstrated (Synthesis, 1974, 90 et seq.), phosphorous acid triesters form 4,4,4-trialkoxy-1,3,4-dioxaphospholanes with aldehydes at low temperature, and predominantly 2,2,2-trialkoxy-1,3,2-dioxaphospholanes at elevated temperature. Both classes of compounds are catalytically inactive; their formation influences the ratio of rhodium to phosphite in the catalyst system and, in this way, leads to a reduction in the activity of the hydroformylation catalyst.

BRIEF DESCRIPTION OF THE INVENTION

It is therefore the object of the present invention to develop a process for the hydroformylation of olefinically unsaturated compounds in which rhodium is employed as the catalyst, in combination with those compounds of trivalent phosphorus which combine the advantage of organic phosphines—low tendency to react with the constituents of the reaction mixture—with those of organic phosphites—high activity even at low temperatures.

This object is achieved by a process for the preparation of aldehydes by reactions of olefinically unsaturated compounds with carbon monoxide and hydrogen in the homogeneous phase at 20° to 150° C. under 0.1 to 20 MPa pressure in the presence of a catalyst system containing rhodium and an organic phosphorus compound. It comprises employing an ammonium salt, which is soluble in organic media, of a sulfonated phosphorus acid triester as the organic phosphorus compound and having at least 2 mol of phosphorus compound per gram atom of rhodium present in the catalyst system.

Surprisingly, the organic phosphorus compounds employed according to the invention do not undergo side reactions during the catalytic reaction of olefinically unsaturated compounds with carbon monoxide and hydrogen. The catalyst therefore retains its activity unchanged over a very long period of time.

DETAILED DESCRIPTION OF THE INVENTION

The ammonium salts of sulfonated phosphorous acid triesters can be derived from phosphorous acid by esterification with the ammonium salts of hydroxysulfonic acids of the Formula

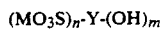

$$(MO_3S)_n\text{-}Y\text{-}(OH)_m \qquad \qquad I$$

In this formula, Y is an organic radical. It accordingly includes sulfonated hydroxy compounds which are derived from aliphatic, cycloaliphatic, aromatic, and heterocyclic structures. The aliphatic compounds can be straight or branched chain and, like the cycloaliphatic compounds, saturated or unsaturated. The cycloaliphatic and the aromatic compounds include both mononuclear and polynuclear structures. The hydroxysulfonic acids of the phosphites likewise include aliphatic-aromatic and also aromatic-aliphatic compounds. Possible heterocyclic compounds are saturated or unsaturated five- or six-membered rings containing nitrogen, oxygen, or sulfur as the hetero atom. The molecule can also contain two identical or different hetero atoms. The heterocyclic ring can moreover be fused to a further heterocyclic five- or six-membered ring or to a benzene ring. All the compounds can also carry further substituents which the expert knows to be inert in the reaction.

Particularly useful as Y in Formula I, are straight or branched chain saturated aliphatic radicals having 2 to 20 carbon atoms, mono- or dinuclear cycloaliphatic radicals having 5 to 12 carbon atoms, or mono- or dinuclear aromatic radicals. The aromatic radicals are preferably derived from benzene, biphenyl, naphthalene, and binaphthyl. The readily available benzyl radical has proven most suitable as the alkylaryl radical. Arylalkyl radicals are preferably based on toluene, ethylbenzene, and the isomeric xylenes. Of the heterocyclic radicals, those of nitrogen-containing saturated or unsaturated five- or six-membered rings are of importance, in particular pyridine. Finally, m is an integer from 1 to 3 and n is an integer from 1 to 4.

M is an ammonium ion of the Formula

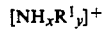

$$[NH_xR^1_y]^+ \qquad \qquad II$$

in which x is 1 or 2, y is 2 or 3, and the sum of x and y is 4. The $R^1$'s are independently aliphatic, cycloaliphatic, aromatic, araliphatic, or heterocyclic radicals. The $R^1$'s are preferably a straight or branched chain alkyl radical, and the sum of all the carbon atoms in the y radicals $R^1$ is 4 to 60. Preferably, when y is 2, the sum of the carbon atoms in the radicals $R^1$ is 12 to 36 and, in particular, 14 to 26. If y is 3, the sum of the carbon atoms is preferably 18 to 42, particularly 21 to 39. Compounds in which $R^1$'s are n-octyl, i-octyl, i-nonyl, i- decyl, and/or i-tridecyl radicals are particularly suitable.

Important ammonium salts of sulfonated phosphorus acid triesters which may be employed according to the invention correspond to the Formula

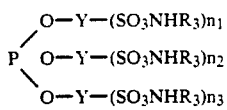   III in which the Y's independently have the meaning given in Formula I. The symbols $n_1$, $n_2$, and $n_3$ are independently integers from 0 to 4, provided that at least one is not 0. The R's are also independently aliphatic, cycloaliphatic, aromatic, araliphatic, or heterocyclic radicals. R is preferably a straight or branched chain alkyl radical, with the three radicals R being joined to the sulfonic acid radical via a nitrogen atom and totaling 10 to 60, preferably 12 to 36, carbon atoms.

The compounds corresponding to the Formula III include ammonium sulfonates of trialkyl phosphites, such as trimethyl phosphite, triethyl phosphite, butyl diethyl phosphite, tri-n-propyl phosphite, tri-n-butyl phosphite, tri-2-ethylhexyl phosphite, tri-n-octyl phosphite and tri-n-dodecyl phosphite. They also include dialkyl aryl phosphites, such as dimethyl phenyl phosphite and diethyl phenyl phosphite; alkyl diaryl phosphites, such as methyl diphenyl phosphite and ethyl diphenyl phosphite; and triaryl phosphites, such as triphenyl phosphite and trinaphthyl phosphite. The preferred phosphite of this group is triphenyl phosphite-trisulfonic acid triisooctyl-ammonium salt.

Another group of important ammonium salts of sulfonated phosphorous acid triesters is represented by Formula IV.

$$(R_3HNO_3S)_{n_1}-Y\begin{matrix}O\\ \\O\end{matrix}P-O-Y-(SO_3NHR_3)_{n_1}$$

In this Formula, the Y's are independently the same as in Formula I, and are preferably radicals which are derived from benzene, biphenyl, naphthalene, or binaphthyl. The $R_2$'s and $n_1$'s are the same as in Formula III.

The preferred ammonium sulfonates of phosphites according to Formula IV are

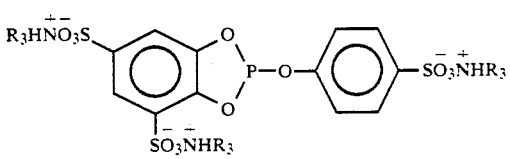

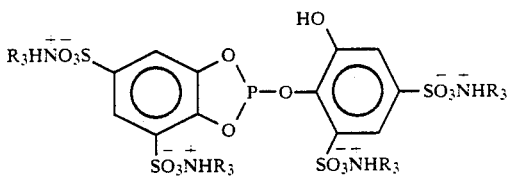

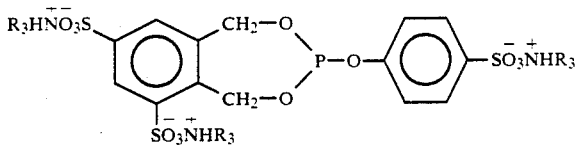

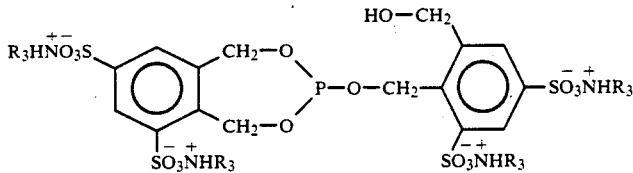

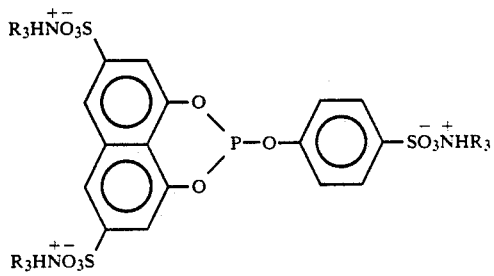

-continued
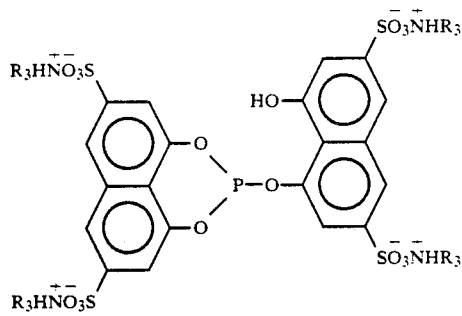
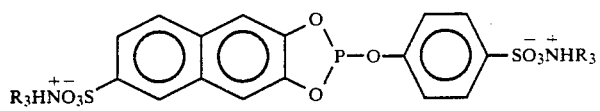
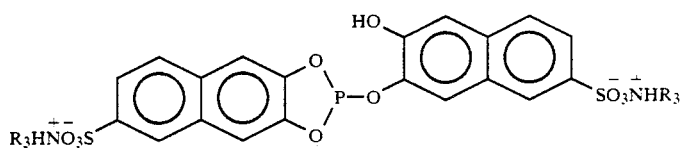
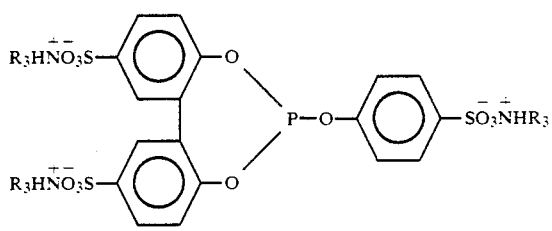
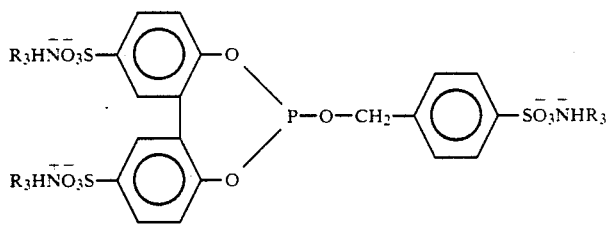
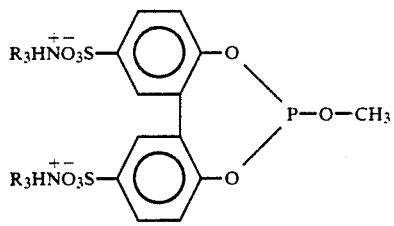
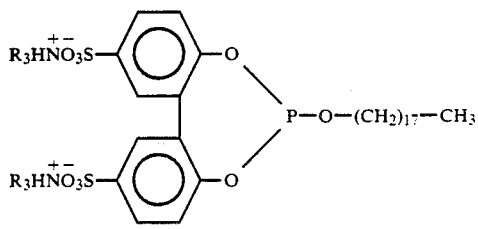

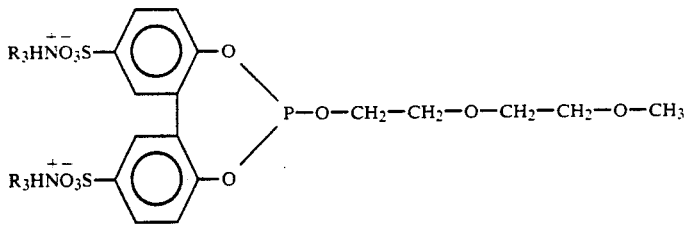

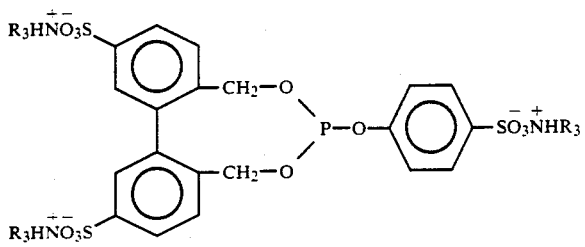

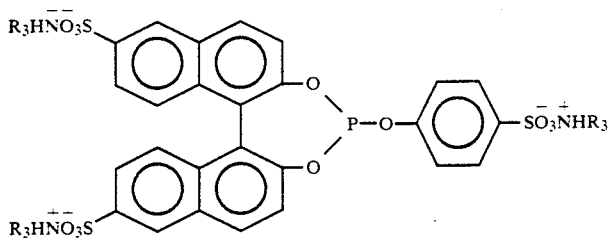

Ammonium salts of sulfonated phosphorous acid triesters of the Formula V are also important.

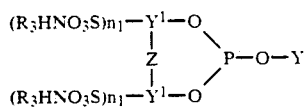

In this Formula, Y, the $R_3$'s, and $n_1$, are the same as in Formula III, and the $Y^1$'s are independently arylalkyl, alkylaryl, aryl, biaryl, naphthyl, or binaphthyl radicals, in particular the benzene radical. Z is —$CH_2$—, —$(CH_2)_2$— or —$(CH_2)_3$—.

Preferred ammonium sulfonates of phosphites according to Formula V are:

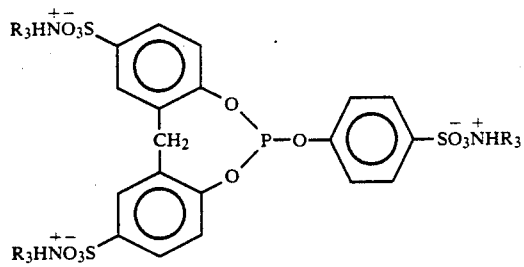

-continued

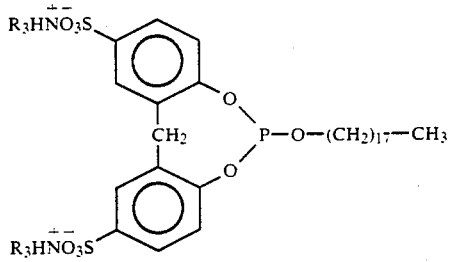

Finally, ammonium salts of sulfonated phosphorous acid triesters of the Formula VI are also of great importance.

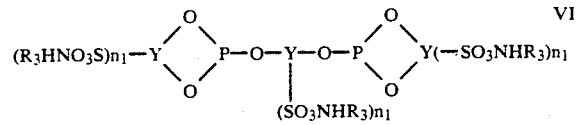

The Y's are independently the same as in Formula I, in particular those which are derived from benzene, biphenyl, or naphthalene, as well as from alkanes having 2 to 6 carbon atoms. The R's and $n_1$ are in accordance with Formula III.

The preferred ammonium sulfonates of phosphites corresponding to the Formula VI are:

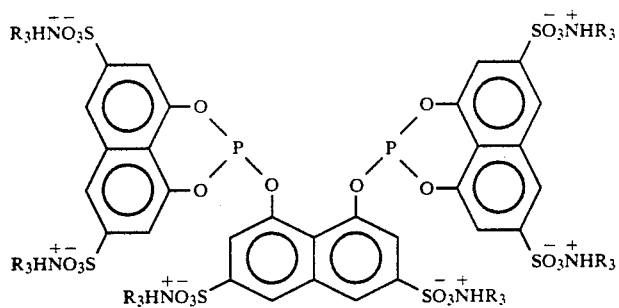
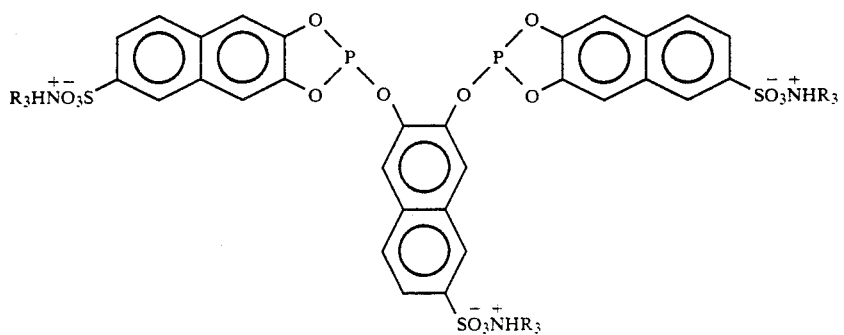
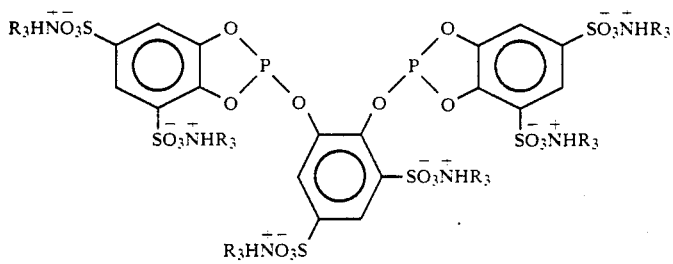
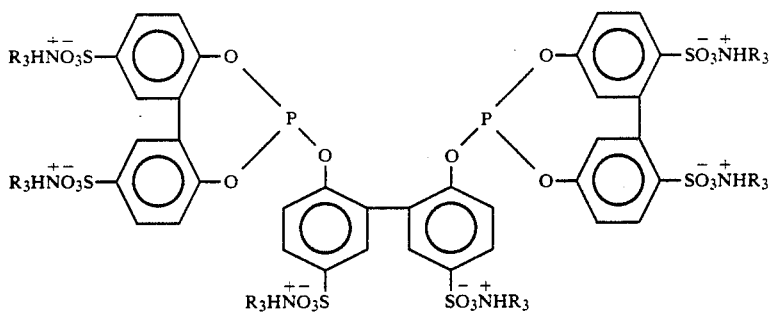
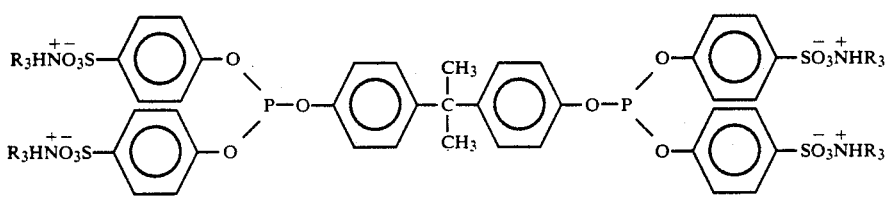

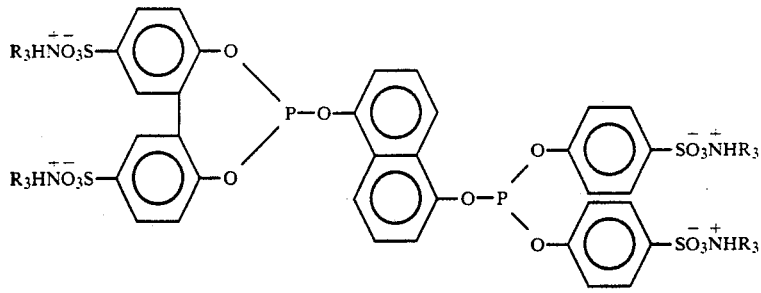

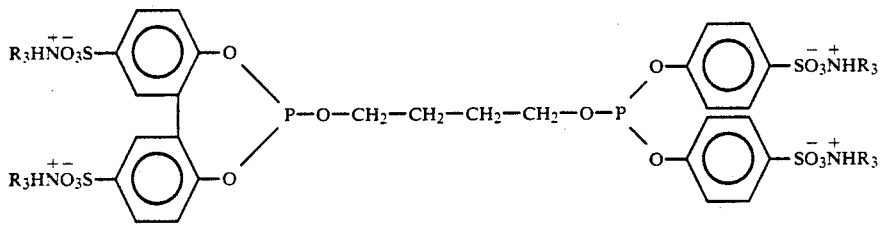

The ammonium salts of sulfonated phosphorous acid triesters according to the invention can be obtained by transesterification (alcoholysis) of phosphorous acid triesters with the ammonium salt of a hydroxysulfonic acid. For this reaction, the ammonium salt is dissolved in an organic solvent and reacted with the phosphorous acid triester at 20° to 200° C., preferably 80° to 160° C. The reactants are usually employed in equivalent amounts, although it is also possible for one of the two reactants to be used in excess. The reaction is accelerated by catalysts, such as amines, sodium, sodium alcoholates, aluminum trichloride, titanic acid esters, or phosphorous acid dialkyl esters. Compounds which are derived from aliphatic or aromatic hydroxy compounds, preferably those containing 1 to 12 carbon atoms, have proven to be suitable phosphorous acid triesters. Examples of such phosphites are trimethyl phosphite, triethyl phosphite, n-butyl diethyl phosphite, tri-n-propyl phosphite, tri-n-butyl phosphite, tri-2-ethyl hexyl phosphite, tri-n-octyl phosphite, tri-n-dodecyl phosphite, dimethyl phenyl phosphite, diethyl phenyl phosphite, and triphenyl phosphite. The preferred organic phosphite is triphenyl phosphite.

The second component of the catalyst system, the rhodium, can be employed either as the metal, preferably on a support such as active charcoal, calcium carbonate, alumina, or similar substrates, or as a rhodium compound. Rhodium compounds which dissolve in organic media under the reaction conditions are suitable. Examples of inorganic or organic rhodium compounds, in which the rhodium can be present in various oxidation stages, are the rhodium oxides $Rh_2O$, $Rh_2O_3$, $RhO_2$, and $RhO_3$; the salts of inorganic hydrogen acids, such as the chlorides, bromides, iodides, sulfides, selenides, and tellurides, e.g. $RhCl_3$, $RhBr_3$, $RhI_3$, $Rh_2S_3$, $Rh_2Se_5$ and $Rh_2Te_5$; the salts of inorganic oxygen acids, such as rhodium sulfite $Rh_2(SO_3)_3$, rhodium sulfate $Rh_2(SO_4)_3$, rhodium nitrate $Rh(NO_3)_3$, rhodium perchlorate $Rh(OH)_2ClO_4$, and rhodium selenate; and salts of aliphatic mono- or polycarboxylic acids, such as rhodium acetate $Rh(CH_3CO_2)_3$, rhodium propionate, rhodium oxalate $Rh_2(C_2O_4)_3$, rhodium malonate, and rhodium 2-ethylhexanoate. Salts of heteropolyacids containing rhodium may also be used; e.g. salts with alkali metals, alkaline earth metals, ammonium, and amines. Specifically noted are sodium hexachlororhodate $Na_3(RhCl_6)$, potassium hexachlororhodate $K_3(RhCl_6)$, barium hexachlororhodate $Ba_3(RhCl_6)_2$, ammonium hexachlororhodate $(NH_4)_3[RhCl_6]$, sodium hexabromorhodate $Na_3(RhBr_6)$, monomethylammonium pentachlororhodate $(NH_3CH_3)_2(RhCl_5)$, and trimethylammonium hexachlororhodate $[NH(CH_3)_3][RhCl_6]$. Carbonyl and halogenocarbonyl compounds of rhodium, such as tricarbonylrhodium $Rh(CO)_3$, tetracarbonylrhodium $[Rh(CO_4)]_2$, tetrarhodium-dodecacarbonyl $Rh_4(CO)_{12}$, $[Rh(CO)_2Cl]_2$, dicarbonylrhodium bromide $[Rh(CO)_2]Br$, and dicarbonylrhodium iodide $[Rh(CO)_2]I$, have also proven suitable.

In addition to simple salts, complex salts of rhodium, in particular of trivalent rhodium, can also be used as the catalyst precursor. These compounds contain mono-, bi-, or tridentate ligands, e.g. $\beta$-diketones, such as acetylacetone, alkylamines, alkyl diamines, and aryldiamines; nitrogen-containing heterocyclic compounds, e.g. pyridine, 2,2'-dipyridine, and 1,10-phenanthroline; and aliphatic or cycloaliphatic and diethylenically unsaturated hydrocarbons, e.g. cyclopentadiene and 1,5-cyclooctadiene.

Rhodium compounds which are particularly suitable for use in the process of the invention are $Rh_4(CO)_{12}$, $Rh_6(CO)_{16}$, $Rh(CO)_3$, $[Rh(CO)_4]_2$, $[Rh(CO)_2Cl]_2$, rhodium 2-ethylhexanoate, rhodium (III) acetylacetonate, rhodium (I) dicarbonylacetylacetonate, cyclooctadienyl rhodium chloride $[Rh(C_8H_{12})Cl]_2$, rhodium acetate $Rh(CH_3CO_2)_3$, $[Rh(OCOCH_3)_2 H_2O]_2$, rhodium nitrate $Rh(NO_3)_3$ and rhodium oxide $Rh_2O_3$.

The catalyst can be prepared beforehand as a solution and then introduced into the reaction zone. For example, the desired amount of rhodium is added to an organic solution of the sulfonated phosphite and the starting substances are allowed to react with one another in the presence of synthesis gas under elevated pressure and temperature. It is also possible for rhodium as metal or a compound and the sulfonated phosphite to be dissolved or suspended in a suitable organic medium and for the catalyst solution to be prepared in situ by simple mixing of these components.

The concentration of the rhodium in the reaction mixture, which essentially consists of olefin, dissolved synthesis gas, reaction product, catalyst and, if appropriate, solvent, is 5 to 500 ppm, preferably 10 to 150 ppm, based on the reaction mixture. The ammonium salt of the sulfonated phosphite is employed in a ratio of 2:1 to 200:1, preferably 10:1 to 100:1 mol of phosphite salt per gram atom of rhodium.

The hydroformylation of the olefinic compounds is carried out at 20° to 150° C., in particular from 50° to 120° C., under 0.1 to 20 MPa, in particular 1 to 10 MPa. The content of olefinic compound in the reaction medium is not critical.

The reaction conditions to be used in individual cases also depend on the nature of the olefinic compound. Reactive starting substances can be reacted at relatively low temperatures and pressures in the presence of small amounts of catalyst, whereas compounds which are slower to react require correspondingly more intense reaction conditions. Examples of reactive olefins are n-hexene-1, n-octene-1, n-decene-1, n-dodecene-1, n-tetradecene-1, and styrene. Examples of olefins which are slow to react are n-octene-4, tripropylene, tetrapropylene, dicyclopentadiene, and limonene.

The olefinic compound can be fed to the hydroformylation as such or in solution. Suitable solvents are ketones, such as acetophenone, acetone, or methyl ethyl ketone; lower aliphatic nitriles, such as acetonitrile, propionitrile, or benzonitrile; dimethylformamide; linear or branched aliphatic saturated monohydroxy compounds, such as methanol, ethanol, propanol, and isopropanol; aromatic hydrocarbons, such as benzene or toluene; and saturated cycloaliphatic hydrocarbons, such as cyclopentane or cyclohexane.

It has been found that the pH of the reaction mixture may fall during the reaction, especially if it contains traces of water or if halogen-containing rhodium compounds are employed. The pH of the reaction mixture should advantageously be not less than 2. The pH is generally brought to 2 to 13, preferably from 4 to 8. The pH which is advantageous for the particular reaction is achieved by addition of a certain amount of a basic compound soluble in an organic medium, for example by addition of amines.

The composition of the synthesis gas can be varied within wide limits. In general, a mixture in which the volume ratio of carbon monoxide to hydrogen is 5:1 to 1:5 is employed. This ratio is advantageously 1:1 or deviates only slightly from this value.

This process can be carried out either batchwise or continuously. It is applied successfully for the hydroformylation of the most diverse olefinically unsaturated compounds. Aliphatic, cycloaliphatic, or araliphatic compounds which have 2 to 20 carbon atoms, possess one or more olefinic double bonds, and optionally contain functional groups can accordingly be reacted. Examples of aliphatic compounds are straight or branched chain alpha-olefins having 2 to 20 carbon atoms, such as ethylene, propylene, butene-1, iso-butylene, pentene-1, 2-methyl-butene-1, hexene-1, heptene-1, octene-1, 2,4,4-trimethylpentene-1, nonene-1, 2-propylhexene-1, decene-1, undecene-1, dodecene-1, n-tetradecene-1, octadene-1, eicosene-1, 3-methylbutene-1, 3-methyl-pentene-1, 3-ethyl-4-methylpentene-1, 3-ethylhexene-1, 4,4-dimethylnonene-1, and 6-propyldecene-1.

Other suitable compounds include acyclic terpenes; branched olefins, such as diisobutylene, tripropylene, tetrapropylene, dimersol; and aliphatic dienes, such as 1,3-butadiene, 1,5-hexadiene and 1,9-decadiene. Examples of useful araliphatic olefins are styrene, alphamethylstyrene, 1,1-diphenylethylene, divinylbenzene, and m-hexylstyrene.

Among the operable cycloaliphatic starting substances are, for example, cyclooctadiene; dicyclopentadiene; and cyclic terpenes, such as limonene, pinene, camphorene, and bisabolene.

Examples of olefinic compounds containing functional groups are allyl compounds, in particular the alcohols and esters, such as allyl alcohol, allylcyclohexane, allylbenzene, 1-allyl-4-vinylbenzene, allyl ethyl ether, allyl t-butyl ether, allyl phenyl ether, and allyl acetate; vinyl compounds, in particular esters and ethers, such as vinyl methyl ether, vinyl ethyl ether, β-vinylnaphthalene, o-vinyl-p-xylene, and vinyl acetate; acrylic acid derivatives, in particular the esters, such as methyl acrylate, ethyl acrylate, and n-propyloctene-7-oate; methacrylic acid derivatives, in particular the esters, such as methyl methacrylate; hex-1-en-4-ol and oct-1-en-4ol; acrolein and acrolein derivatives, such as acrolein dimethyl and diethyl acetals; cyano compounds, in particular acrylonitrile; and unsaturated ketones, such as vinyl ethyl ketone.

Internal olefins, having 4 to 20 carbon atoms of the formula $R^4R^5C=CR^6R^7$, are particularly successfully hydroformylated by the novel process. $R^4$ and $R^6$ independently are a H atom or an organic radical and together can also form a cycloaliphatic, aromatic, or heterocyclic ring; $R^5$ and $R^7$ independently are an organic radical or together can form an aliphatic, cycloaliphatic, aromatic, or heterocyclic ring.

Internal olefins which are free from halogen and sulfur are preferred. Examples are cis- and trans-butene-2, 2-methylpropene, 2-methylbutene-2, 2,3-dimethylbutene-2, 1,2-diphenylethylene, hexene-2, hexene-3, cis- and trans-heptene-2, octene-2, octene-3, octene-4, 3-methylheptene-2, 3-methylheptene-3, 3-methylheptene-5, 3,4-dimethylhexene-2, decene-2, tetradecene-2, 4-amyldecene-2, 4-methyltridecene-2, octadecene-2, 6,6-dipropyldecene-3, propenyl-1-benzene, 3-benzylheptene-3, cyclobutene, cyclopentene, cyclohexene, cycloheptene, cyclooctene, 1-methylcyclohexene, diethyl maleate, diethyl fumarate, crotonaldehyde, crotonaldehyde dimethyl acetal, ethyl cinnamate, and cis- and trans-propene-1-yl t-butyl ether.

The following examples illustrate the invention without limiting it to the embodiments described. The following abbreviations are used in the examples below:
TPP: triphenylphosphine
TPPp: triphenyl phosphite
TPPpS: triphenyl phosphite-sulfonic acid
TPPpTS: triphenyl phosphite-trisulfonic acid
TPPpDS: triphenyl phosphite-disulfonic acid
TPPpMS: triphenyl phosphite-monosulfonic acid
TIOA: triisooctylamine TPPpS-TIOA in the following examples is understood to be mixture of 21% by weight of TPPpMS-TIOA, 46% by weight of TPPpDS-TIOA, and 33% by weight of TPPpTS-TIOA.

EXPERIMENTAL PROCEDURE

All experiments are carried out in a high grade steel autoclave provided with a stirring device and inlet connectors. To remove the oxygen, the autoclave is evacuated, filled with argon and heated to the particular reaction temperature. Synthesis gas is then forced in and the autoclave is let down again several times. The prepared catalyst solution, n-tetradecene-1 and one third of the calculated amount of the solvent acetophenone is subsequently introduced into the autoclave. The autoclave is fitted with a pressure sensor which enables the decrease in pressure during the reaction to be monitored continuously and recorded by means of a pen.

The catalyst solution is prepared in a Schlenk tube which has been evacuated, heated thoroughly, and filled with argon. The calculated amount of phosphorous compound, dissolved in two thirds of the total amount of acetophenone, followed by the calculated amount of rhodium, as Rh 2-ethylhexanoate, are charged into this vessel. The contents of the autoclave are brought to the desired reaction pressure at the reaction temperature by forcing in synthesis gas ($CO/H_2 = 1:1$) and then stirred.

When the reaction has ended (3 hours), the autoclave is cooled to about 25° C., the excess gas is released and the contents of the reactor are discharged and analyzed by gas chromatography.

The reaction conditions and the results are summarized in the tables.

EXAMPLE 1

Hydroformylation of n-tetradecene-1 in the presence of a rhodium 2-ethylhexanoate/TPPpS-TIOA catalyst.

Reaction conditions:
125° C., 0.6 MPa, reaction time of 3 hours, $CO/H_2 = 1:1$, and pH = 4.2–4.7.

20 g (=0.098 mol) of n-tetradecene (94.1% of n-tetradecene-1, 2.5% of other n-tetradecene isomers) and 190.47 mg of 1.05% rhodium 2-ethylhexanoate solution (solvent xylene), i.e. 2 mg (=0.0194 mmol) of rhodium; rhodium concentration: 50 ppm are mixed into Experiment 1/1: 0.2389 g (=0.1943 mmol) of TPPpS-TIOA in 17.66 g of acetophenone,
1/2: 0.4778 g (=0.3886 mmol) of TPPps-TIOA in 17.24 g of acetophenone,
1/3: 0.9556 g (=0.7772 mmol) of TPPpS-TIOA in 16.45 g of acetophenone,
1/4: 1.8985 g (=1.544 mmol) of TPPpS-TIOA in 15.02 g of acetophenone,
1/5: 2.3891 g (=1.943 mmol) of TPPps-TIOA in 14.04 g of acetophenone.

The details of the reaction and the results thereof are set forth in Table 1.

TABLE 1

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 1/1 | 10 | 34 | 33.8 | 79.52 | 19.7 | 0.7 | — | — | — | 80/20 |
| 1/2 | 20 | 34 | 33.9 | 82.2 | 17.5 | 0.2 | — | — | — | 82/18 |
| 1/3 | 40 | 30 | 29.8 | 84.8 | 15.2 | — | — | — | — | 85/15 |
| 1/4 | 80 | 9 | 8.0 | 85.9 | 14.0 | — | — | — | — | 86/14 |
| 1/5 | 100 | 7 | 6.9 | 88.1 | 11.8 | — | — | — | — | 88/12 |

EXAMPLE 2 (COMPARISON)

Hydroformylation of n-tetradecene-1 in the presence of rhodium 2-ethylhexanoate/TPP as the catalyst.

In order to obtain a direct comparison between TPPpS-TIOA and TPP as co-catalysts, the reaction is carried out in accordance with Example 1 except that the tetradecene and rhodium 2-ethylhexanoate are mixed into Experiment 2/1: 0.0509 g (=0.1943 mmol) of TPP in 17.9 g of acetophenone,
2/2: 0.1019 g (=0.3886 mmol) of TPP in 17.6 g of acetophenone,
2/3: 0.2038 g (=0.7772 mmol) of TPP in 17.8 g of acetophenone,
2/4: 0.4077 g (=1.5544 mmol) of TPP in 17.2 g of acetophenone,
2/5: 0.5096 g (=1.943 mmol) of TPP in 17.4 g of acetophenone.

The details of the reaction and the results thereof are set forth in Table 2.

TABLE 2

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 2/1 | 10 | 41 | 40.9 | 66.5 | 29.2 | 2.9 | 0.93 | 0.28 | 0.14 | 67/33 |
| 2/2 | 20 | 43 | 42.9 | 71.0 | 26.7 | 1.7 | 0.48 | | 0.11 | 71/29 |
| 2/3 | 40 | 49 | 48.9 | 73.1 | 24.8 | 1.4 | 0.4 | | 0.1 | 73/27 |
| 2/4 | 80 | 47 | 46.8 | 76.5 | 22.4 | 0.8 | 0.1 | | 0.09 | 77/23 |
| 2/5 | 100 | 44 | 43.9 | 77.9 | 21.5 | 0.4 | 0.1 | | | 78/22 |

EXAMPLE 3 (COMPARISON)

Hydroformylation of n-tetradecene-1 in the presence of rhodium 2-ethylhexanoate/TPPp as the catalyst.

n-Tetradecene-1 is hydroformylated with Rh 2-ethylhexanoate and TPPp as the co-catalyst under the conditions of Example 1 in order to compare the action of TPPpS-TIOA and TPPp as co-catalysts, except that the tetradecene and rhodium 2-ethylhexanoate are mixed into Experiment 3/1: 0.060 g (=0.1943 mmol) of TPPp in 17.9 g of toluene,
3/2: 0.1205 g (=0.3886 mmol) of TPPp in 18.0 g of toluene,
3/3: 0.2411 g (=0.7772 mmol) of TPPp in 17.9 g of toluene,
3/4: 0.4823 g (=1.5544 mmol) of TPPp in 17.4 g of toluene,
3/5: 0.6029 g (=1.943 mmol) of TPPp in 17.5 g of toluene.

The details of the reaction and the results thereof are set forth in Table 3.

TABLE 3

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 3/1 | 10 | 23 | 22.9 | 66.42 | 27.6 | 3.7 | 1.5 | 0.5 | 0.27 | 66/34 |
| 3/2 | 20 | 35 | 34.9 | 78.8 | 20.4 | 0.7 | 0.1 | | — | 79/21 |
| 3/3 | 40 | 47 | 46.8 | 79.7 | 19.5 | 0.6 | 0.1 | | — | 80/20 |
| 3/4 | 80 | 46 | 45.8 | 80.1 | 19.3 | 0.4 | 0.1 | | — | 80/20 |
| 3/5 | 100 | 32 | 31.9 | 82.2 | 17.6 | 0.1 | 0.1 | | — | 82/18 |

EXAMPLE 4

Hydroformylation of n-tetradecene-1 in the presence of rhodium 2-ethylhexanoate/TPPpS-TIOA as the catalyst.

The hydroformylation of n-tetradecene-1 is carried out under the conditions of Example 1 but at pH 6 except that the tetradecene and 2-ethylhexanoate are mixed into
Experiment
4/1: 0.3131 g (=0.1943 mmol) of TPPps-TIOA in 17.4 g of acetophenone,
4/2: 0.6262 g (=0.3886 mmol) of TPPpS-TIOA in 17.2 g of acetophenone,
4/3: 1.2524 g (=0.7772 mmol) of TPPpS-TIOA in 16.1 g of acetophenone,
4/4: 2.5049 g (=1.544 g) of TPPpS-TIOA in 14.4 g of acetophenone,
4/5: 3.1311 g (=1.943 mmol) of TPPpS-TIOA in 13.8 g of acetophenone.

The pH is brought to 6.0 by addition of 0.1 to 0.27 g of TIOA. The details of the reaction and the results thereof are set forth in Table 4.

TABLE 4

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 4/1 | 10 | 51 | 50.8 | 73.8 | 22.1 | 2.6 | 1.0 | 0.4 | 0.2 | 74/26 |
| 4/2 | 20 | 48 | 47.9 | 77.2 | 20.5 | 1.7 | 0.4 | | 0.2 | 77/23 |
| 4/3 | 40 | 50 | 49.8 | 83.3 | 16.1 | 0.4 | 0.2 | | — | 83/17 |
| 4/4 | 80 | 22 | 21.9 | 83.4 | 16.6 | — | — | — | — | 83/17 |
| 4/5 | 100 | 17 | 16.9 | 87.4 | 12.6 | — | — | — | — | 87/13 |

EXAMPLE 5

Hydroformylation of n-tetradecene-1 in the presence of rhodium 2-ethylhexanoate/TPPpS-TIOA as the catalyst.

Example 1 is repeated, with the difference that the rhodium concentration is decreased from 50 to 20 ppm and the pressure is increased from 0.6 MPa to 5.0 MPa.

20 g (=0.098 mol) of n-tetradecene (93.9% of n-tetradecene-1, 2.8% of other n-tetradecene isomers) and 95.23 mg of a 1.05% rhodium 2-ethylhexanoate solution (solvent xylene), i.e. 1 mg (=0.00971 mmol) of Rh, rhodium concentration: 20 ppm, are mixed into
Experiment
5/1: 0.4775 g (=0.388 mmol) of TPPpS-TIOA in 27.25 g of acetone,
5/2: 0.9551 g (=0.7768 mmol) of TPPpS-TIOA in 27.77 g of acetone.

The acetone used in 5/1 and 5/2 is predried over CaCl₂; the details of the reaction and the results thereof are set forth in Table 5.

TABLE 5

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 5/1 | 40 | 71 | 70.9 | 73.9 | 25.3 | 0.6 | 0.14 | | — | 74/26 |
| 5/2 | 80 | 70 | 69.9 | 74.7 | 24.6 | 0.45 | 0.12 | | — | 75/25 |

EXAMPLE 6 (COMPARISON)

Hydroformylation of n-tetradecene-1 in the presence of rhodium 2-ethylhexanoate/TPP as the catalyst.

In order to compare the activity of TPPpS-TIOA and TPP as co-catalysts, the reaction is carried out as in Example 5. The tetradecene and rhodium 2-ethylhexanoate are mixed into
Experiment
6/1: 0.1018 g (=0.388 mmol) of TPP in 27.76 g of acetone,
6/2: 0.2037 g (=0.7768 mmol) of TPP in 27.92 g of acetone.

The details of the reaction and the results thereof are set forth in Table 6.

TABLE 6

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 6/1 | 40 | 81 | 80.9 | 72.1 | 27.2 | 0.43 | 0.14 | | — | 72/28 |
| 6/2 | 80 | 83 | 82.0 | 72.4 | 27.1 | 0.31 | 0.13 | | — | 72/28 |

EXAMPLE 7

Hydroformylation of n-tetradecene-1 in the presence of rhodium 2-ethylhexanoate/TPPpS-TIOA as the catalyst.

Example 5 is repeated except that the reaction temperature is 110° C. instead of 125° C. The tetradecene and rhodium 2-ethylhexanoate are mixed into Experiment 7/1: 0.4775 g (=0.3884 mmol) of TPPpS-TIOA in 27.02 g of acetone, 7/2: 0.9551 g (=0.7768 mmol) of TPPpS-TIOA in 26.7 g of acetone.

The details of the reaction and the results thereof are set forth in Table 7

TABLE 7

| Experiment No. | P/Rh ratio (in mol) | Conversion (%) | Aldehyde yield | Selectivity (%) | | | | | n/i ratio |
|---|---|---|---|---|---|---|---|---|---|
| | | | | al-1 | al-2 | al-3 | al-4 | al-5/6 | |
| 7/1 | 40 | 90 | 89.9 | 67.7 | 29.4 | 2.1 | 0.49 | 0.15 | 68/32 |
| 7/2 | 80 | 88 | 87.9 | 70.8 | 28.1 | 0.8 | 0.1 | | 71/29 |

EXAMPLE 8 (COMPARISON)

Hydroformylation of n-tetradecene-1 in the presence of rhodium 2-ethylhexanoate/TPP as the catalyst.

To compare the activity of TPPpS-TIOA and TPP as co-catalysts at lower temperatures, the reaction is carried out as in Example 7. The tetradecene and rhodium 2-ethylhexanoate are mixed into Experiment 8/1: 0.1018 g (=0.3884 mmol) of TPP in 27.98 g of acetone, 8/2: 0.2037 g (=0.7768 mmol) of TPP in 27.75 g of acetone.

The details of the reaction and the results thereof are set forth in Table 8.

TABLE 8

| Experiment No. | P/Rh ratio (in mol) | Conversion (%) | Aldehyde yield | Selectivity (%) | | | | n/i ratio |
|---|---|---|---|---|---|---|---|---|
| | | | | al-1 | al-2 | al-3 | al-4/5 | |
| 8/1 | 40 | 69 | 68.9 | 72.6 | 27.1 | 0.12 | 0.09 | 73/27 |
| 8/2 | 80 | 63 | 62.9 | 72.6 | 27.1 | 0.1 | 0.1 | 73/27 |

EXAMPLE 9 (COMPARISON)

Hydroformylation of n-tetradecene-1 in the presence of rhodium 2-ethylhexanoate/TPPp as the catalyst.

In this example, the activity of TPPp as a co-catalyst (Examples 7 and 8) in the hydroformylation of n-tetradecene-1 under the conditions of Examples 7 and 8 is investigated. The tetradecene and rhodium 2-ethylhexanoate are mixed into Experiment 9/1: 0.1205 g (=0.388 mmol) of TPPp in 28.03 g of acetone 9/2: 0.2410 g (=0.7768 mmol) of TPPp in 27.82 g of acetone The details of the reaction and results thereof are set forth in Table 9.

TABLE 9

| Experiment No. | P/Rh ratio (in mol) | Conversion (%) | Aldehyde yield | Selectivity (%) | | | | | | n/i ratio |
|---|---|---|---|---|---|---|---|---|---|---|
| | | | | al-1 | al-2 | al-3 | al-4 | al-5 | al-6/7 | |
| 9/1 | 40 | 81 | 80.9 | 71.2 | 27.8 | 0.6 | 0.04 | 0.04 | 0.16 | 71/29 |
| 9/2 | 80 | 77 | 76.9 | 72.7 | 26.9 | 0.2 | 0.1 | | — | 73/27 |

EXAMPLE 10

Hydroformylation of n-hexene-1 in the presence of $Rh_4(CO)_{12}$/TPPpS-TIOA as the catalyst.

Example 1 is repeated, except that n-hexene-1 is employed and the reaction is carried out under 2.5 MPa.

16.66 g (=0.194 mol) of n-hexene (97.07% of n-hexene-1 and 0.87% of other n-hexene isomers); and 1.81 ml of an $Rh_4(CO)_{12}$ solution (300 mg of $Rh_4(CO)_{12}$ in 300 ml of toluene), i.e. 1 mg (=0.00971 mmol) of Rh, rhodium concentration: 20 ppm, are mixed into Experiment 10/1: 0.1194 g (=0.09717 mmol) of TPPpS-TIOA in 29.56 g of acetophenone, 10/2: 0.4779 g (=0.3887 mmol) of TPPpS-TIOA in 27.80 g of acetophenone, 10/3: 0.9558 g (=0.7774 mmol) of TPPpS-TIOA in 26.20 g of acetophenone, 10/4: 1.1948 g (=0.9717 mmol) of TPPpS-TIOA in 25.86 g of acetophenone.

The details of the reaction and the results thereof are set forth in Table 10.

TABLE 10

| Experiment No. | P/Rh ratio (in mol) | Conversion (%) | Aldehyde yield | Selectivity (%) | | | n/i ratio |
|---|---|---|---|---|---|---|---|
| | | | | n-heptanal | 2-methyl-hexanal | 2-ethyl-pentanal | |
| 10/1 | 10 | 89 | 88.7 | 60.0 | 32.3 | 7.5 | 60/40 |
| 10/2 | 40 | 88 | 87.4 | 75.5 | 23.0 | 1.4 | 76/24 |
| 10/3 | 80 | 90 | 89.9 | 78.6 | 20.6 | 0.7 | 79/21 |
| 10/4 | 100 | 82 | 81.7 | 79.9 | 19.6 | 0.4 | 80/20 |

EXAMPLE 11 (COMPARISON)

Hydroformylation of n-hexene-1 in the presence of $Rh_4(CO)_{12}$/TPP as the catalyst.

In order to compare the activity of TPPpS-TIOA and TPP as co-catalysts, the reaction is carried out as in Example 10. The tetradecene and rhodium carbonyl are mixed into Experiment 11/1: 0.025 g (=0.09717 mmol) of TPP in 30.25 g of toluene, 11/2: 0.1019 g (=0.3887 mmol) of TPP in 29.90 g of toluene, 11/3: 0.2548 g (=0.9717 mmol) of TPP in 29.80 g of toluene.

The details of the reaction and the results thereof are set forth in Table 11.

TABLE 11

| Experiment No. | P/Rh ratio (in mol) | Conversion (%) | Aldehyde yield | Selectivity (%) | | | n/i ratio |
|---|---|---|---|---|---|---|---|
| | | | | n-heptanal | 2-methyl-hexanal | 2-ethyl-pentanal | |
| 11/1 | 10 | 89 | 88.5 | 67.5 | 29.5 | 2.9 | 68/32 |
| 11/2 | 40 | 86 | 85.7 | 72.3 | 27.1 | 0.6 | 72/28 |
| 11/3 | 100 | 85.5 | 85.4 | 74.6 | 25.3 | 0.1 | 75/25 |

EXAMPLE 12 (COMPARISON)

Hydroformylation of n-hexene-1 in the presence of $Rh_4(CO)_{12}$/TPPp as the catalyst.

The n-Hexene-1 is hydroformylated with $Rh_4(CO)_{12}$ and triphenyl phosphite (TPPp) as the co-catalyst under the same conditions as in Examples 10 and 11 in order to compare the activity of TPPpS-TIOA and TPP as the co-catalyst. The n-hexene and $Rh_4(CO)_{12}$ are mixed into Experiment 12/1: 0.030 g (=0.0971 mmol) of TPPp in 30.0 g of toluene, 12/2: 0.120 g (=0.3887 mmol) of TPPp in 29.8 g of toluene, 12/3: 0.301 g (=0.9717 mmol) of TPPp in 26.5 g of toluene.

The details of the reaction and results thereof are set forth in Table 12.

TABLE 12

| Experiment No. | P/Rh ratio (in mol) | Conversion (%) | Aldehyde yield | Selectivity (%) | | | n/i ratio |
|---|---|---|---|---|---|---|---|
| | | | | n-heptanal | 2-methyl-hexanal | 2-ethyl-pentanal | |
| 12/1 | 10 | 65 | 65 | 45.5 | 41.3 | 13.2 | 45/55 |
| 12/2 | 40 | 92 | 91.7 | 67.6 | 27.9 | 4.4 | 68/32 |
| 12/3 | 100 | 87 | 87 | 74.4 | 23.7 | 1.9 | 74/26 |

What we claim is:

1. A process for the preparation of an aldehyde by reaction of an olefinically unsaturated compound with carbon monoxide and hydrogen in a homogeneous phase at 20° to 150° C. under 0.1 to 20 MPa in the presence of a catalyst system containing rhodium and an organic phosphorus compound, wherein said organic phosphorous compound is a salt of an ammonium ion and a sulfonated phosphorous acid triester, there being at least 2 mols of said phosphorus compound per gram atom of rhodium present in the catalyst system, said ammonium salt being soluble in organic media.

2. The process of claim 1 wherein said phosphorous acid triester has an alcohol component of the formula $$(MO_3S)_n-Y-(OH)_m \qquad \text{I}$$

wherein Y is an organic radical, M is an ammonium ion, m is an integer from 1 to 3, and n is an integer from 1 to 4.

3. The process of claim 2 wherein Y is a radical selected from the group consisting of straight and branched chain aliphatics having 2 to 20 carbon atoms, mono- and dinuclear cycloaliphatics having 5 to 12 carbon atoms, mono- and dinuclear aromatics, alkylaryls, arylalkyls, and nitrogen-containing, saturated and unsaturated heterocyclic five and six membered rings.

4. The process of claim 3 wherein said dinuclear aromatics are derivatives of benzene, biphenyl, naphthalene, or binaphthyl, said alkylaryls are derivatives of toluene, ethylbenzene, or xylenes, and said rings are pyridine.

5. The process of claim 2 wherein said ammonium ion is of the formula $$[NH_xR^1_y]$$

wherein x is 1 or 2, y is 2 or 3, the sum of x and y is 4, and radicals $R^1$ are independently selected from the group consisting of aliphatics, cycloaliphatics, aromatics, araliphatics, and heterocyclics.

6. The process of claim 5 wherein said radicals $R^1$ are straight or branched chain alkyls, y is 2, and the sum of all carbon atoms in said $R^1$'s is 4 to 60.

7. The process of claim 6 wherein said sum is 12 to 36.

8. The process of claim 7 wherein said sum is 14 to 26.

9. The process of claim 5 wherein said radicals $R^1$ are straight or branched chain alkyls, y is 3, and the total of all carbon atoms in said radicals $R^1$ is 18 to 42.

10. The process of claim 9 wherein said total is 21 to 39.

11. The process of claim 6 wherein said radicals $R^1$ are selected from the group consisting of n-octyl, i-octyl, i-nonyl, i-decyl, and i-tridecyl.

12. The process of claim 9 wherein said radicals $R^1$ are selected from the group consisting of n-octyl, i-octyl, i-nonyl, i-decyl, and i-tridecyl.

13. The process of claim 1 wherein said triester is of the formula

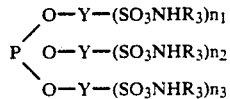

III wherein Y's are independently organic radicals, $n_1$, $n_2$, and $n_3$ are independently an integer from 0 to 4, provided that at least one of said $n_1$, $n_2$, and $n_3$ is at least one, the R's are independently radicals selected from the group consisting of aliphatics, cycloaliphatics, aromatics, araliphatics, and heterocyclics, the sum of said R's being 10 to 60 carbon atoms.

14. The process of claim 13 wherein said R's are independently straight or branched chain alkyls and said sum of said R's is 12 to 36 carbon atoms.

15. The process of claim 1 wherein said triester is of the Formula

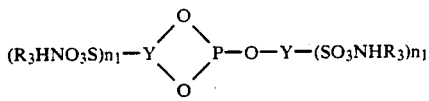
IV wherein said Y's are independently organic radicals, said $n_1$'s are independently integers from 0 to 4 provided that at least one $n_1$ is at least 1, said R's are independently selected from the group consisting of aliphatics, cycloaliphatics, aromatics, araliphatics, and heterocyclics, the sum of said R's being 10 to 60 carbon atoms.

16. The process of claim 15 wherein said Y's are derivatives of benzene, biphenyl, naphthalene, or binaphthyl, said R's are straight or branched chain alkyls and said sum is 12 to 36 carbon atoms.

17. The process of claim 1 wherein triester is of the formula

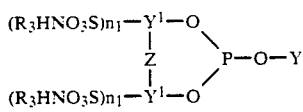
V wherein Y is an organic radical, said $Y^1$'s are independently selected from the group consisting of arylalkyls, alkylaryls, aryls, biaryls, naphthyls, and binaphthyls, Z is $-CH_2-$, $-(CH_2)_2-$, or $-(CH_2)_3-$, said $n_1$'s are an integer from 0 to 4, provided that at least one $n_1$ is at least 1, said R's are independently selected from the group consisting of aliphatics, cycloaliphatics, aromatics, araliphatics, and heterocyclics, the sum of said R's being 10 to 60 carbon atoms.

18. The process of claim 17 wherein the $Y^1$'s are at least one derivative of benzene, biphenyl, naphthalene, or binaphthyl, said R's are straight or branched chain alkyls, said sum being 12 to 36 carbon atoms.

19. The process of claim 1 wherein said triester is of the formula

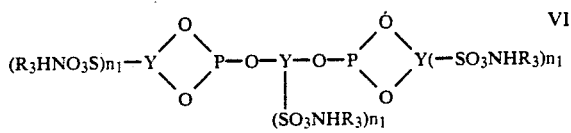
VI wherein said Y's are independently organic radicals, said $n_1$'s are independently integers from 0 to 4, provided that at least one $n_1$ is at least 1, said R's are independently selected from the group consisting of aliphatics, cycloaliphatics, aromatics, araliphatics, and heterocyclics, the sum of said R's being 10 to 60 carbon atoms.

20. The process of claim 19 wherein said Y's are derivatives of benzene, biphenyl, naphthalene, or alkanes having 2 to 6 carbon atoms, said R's are independently straight or branched chain alkyls, said sum being 12 to 36 carbon atoms.

21. The process of claim 1 wherein said rhodium is present in an amount of 5 to 500 ppm based on said unsaturated compound, there being at least 2 mols of said triester per gram atom of rhodium.

22. The process of claim 21 wherein said amount is 10 to 150 ppm.

23. The process of claim 21 wherein 2 to 200 mols of said triester per gram atom of rhodium are present.

24. The process of claim 23 wherein there are 10 to 100 mols of said triester per gram atom of rhodium.

25. The process of claim 1 which is carried out at a temperature of 50° to 120° C. and under a pressure of 1 to 10 MPa.

26. The process of claim 1 carried out at a pH of 2 to 13.

27. The process of claim 26 wherein said pH is 4 to 8.

28. The process of claim 1 wherein the volume ratio of said carbon monoxide to said hydrogen is 5:1 to 1:5.

29. The process of claim 28 wherein said ratio is about 1:1.

* * * * *